United States Patent [19]
Lefevre et al.

[11] Patent Number: 5,138,181
[45] Date of Patent: Aug. 11, 1992

[54] APPARATUS FOR COUNTING AND DETERMINING AT LEAST ONE LEUCOCYTIC SUB-POPULATION

[75] Inventors: Didier Lefevre, Mantes-La-Ville; Henri Champseix, Montesson; Serge Champseix, Les Mureaux, all of France

[73] Assignee: ABX S.A., Montpellier, France

[21] Appl. No.: 602,952

[22] Filed: Oct. 26, 1990

[30] Foreign Application Priority Data

Oct. 27, 1989 [FR] France ................................ 89 14120

[51] Int. Cl.$^5$ .......................... G01N 15/06; G01N 1/10
[52] U.S. Cl. .................................... 250/573; 250/576; 356/246; 356/73
[58] Field of Search ............................ 356/246, 73, 39; 250/573, 574, 576, 222.1

[56] References Cited

U.S. PATENT DOCUMENTS

| | | | |
|---|---|---|---|
| 3,781,112 | 12/1973 | Groner et al. | 356/73 |
| 4,348,107 | 9/1982 | Leif | 356/246 |
| 4,352,558 | 10/1982 | Eisert | 356/73 |
| 4,515,274 | 5/1985 | Hollinger et al. | 356/246 |
| 4,673,289 | 6/1987 | Gaucher | 356/246 |
| 4,997,275 | 3/1991 | Gaucher et al. | 356/246 |
| 5,007,732 | 4/1991 | Ohki et al. | 356/73 |
| 5,030,002 | 7/1991 | North, Jr. | 356/73 |

*Primary Examiner*—David C. Nelms
*Assistant Examiner*—Michael Messinger
*Attorney, Agent, or Firm*—Fleit, Jacobson, Cohn, Price, Holman & Stern

[57] ABSTRACT

An apparatus is disclosed for counting and determining at least one leucocytic sub-population, comprising a case for injecting a flow of sample to be analyzed inside a measurement tank through which a light beam passes, comprising internal and external nozzles for sleeving the sample by means of a pressurized liquid. Electrodes for the resistivity measurements of the leucocytic sub-population are component elements of the injection case. Units for collecting and processing the signals delivered by the optical sensor and the electrodes are also provided.

11 Claims, 3 Drawing Sheets

APPARATUS FOR COUNTING AND DETERMINING AT LEAST ONE LEUCOCYTIC SUB-POPULATION

FIELD OF THE INVENTION

The invention relates to the counting and of at least one leucocytic sub-population and relates more precisely to an apparatus for carrying out such identification by optical and electronic measurement.

BACKGROUND OF THE INVENTION

Independently of the manual method for counting and analysing a leucocytic sub-population which consists in visualising by means of a microscope blood samples spread on a slide, and previously coloured, there exist automatic methods which perform much better and are more accurate for simultaneously differentiating several types of blood populations. Two types of analysis methods are essentially known : the methods of resistivity size analysis and optical analysis methods.

Analysis and automatic counting by resistivity are based on the principle of a cell passing through an electric field where a constant current is maintained. The resistance which this cell opposes in the field causes an increase of the voltage required for the constancy of the current in accordance with Ohm's law. The voltage pulse generated by the passage of this cell is proportional to the resistance opposed, so to its volume without consideration of form. In order to determine a leucocytic sub-population using this principle, it is necessary to treat the blood sample previously with specific cytochemical agents for partially destroying the cells not under consideration, in order to obtain a size discrimination as accurate as the treatment is specific.

The differentiation method the most commonly used with this principle is a method called "leucocytic screening", for obtaining an approximation of the blood formula over three populations : the Lymphocytes, the Mononucleates and the Granulocytes.

The essential part of the analysis is based on the use of a lytic reagent with differential action. Because of this reagent, the membranes of the leucocytes let the contents of the cytoplasm escape. Since the cells have no granules contained in their cytoplasm, they have then the cytoplasmic membrane covering their nucleus; the granulocytes keep a part of the cytosol, their granules partially preventing its escape.

The main drawback of this method resides in the fact that the leucocytes are only differentiated by their final size and that the action of the lysis on certain cells, particularly the eosinophils and the basophils is not completely under control, which frequently causes overlapping, even superimposition of the populations which makes differentiation impossible or very hazardous.

Furthermore, the analysis and counting of a leucocytic sub-population using optical methods is based either on the principle of optical diffraction measurement, or on the principle of measurement of the optical density of a cell, or a combination of the two.

In the first case, a cell passing through a light ray generates diffraction of the incider light, whose intensity at different angles depends on one size of the cell and on the amount of light absorbed thereby. An optical collector having at its center a disc with a black background is placed in the alignment of the optical path. The light transmitted is stopped by the disc whereas the diffracted light is collected on a photosensitive sensor whose response is proportional to the diffraction of the cell.

In the second case, a cell passing through a light ray generates absorbance of the incident light. The transmitted light is filtered at the wavelength corresponding to the coloration of the cell, then is collected by a photosensitive sensor whose response is proportional to the light absorbed at the specified wavelength.

Since the cellular diffraction is related to the absorbance of the cell as well as to its form, measurements of volume remain uncertain, particularly in so far as the leucocytes are concerned, and it is necessary to make the cells to be measured artificially spherical. It can also be noted that a very coloured large sized cell will be seen smaller than its actual size.

Combinations of these principles are used so as to obtain, for the same cell, values of diffraction and coloration intensity or diffraction values at different wavelengths, or else diffraction values at different angles. By means of specific cytochemistries, cellular discrimination can be obtained.

The apparatus using these principles suffer from great sensitivity of the optical alignment which means that the diffraction measurements have only relative stability. Numerous factors also cause the measurement to be fragile such, in particular, as fouling up of the reading tank, the sensitivity of the optical parts to atmospheric dust and to the temperature and hygrometry of the premises. Moreover, the high technicity required for a well performing optical assembly makes the cost of the apparatus unattractive.

SUMMARY OF THE INVENTION

Therefore, the invention provides an apparatus which avoids the drawbacks inherent in apparatus applying the above methods and which makes possible the identification, counting and/or analysis of at least one leucocytic subpopulation and in particular the polynuclear eosinophils.

Thus, the object of the invention resides in an apparatus for counting and determining at least one leucocytic sub-population using at least partially an analysis and counting method by resistivity based on the principle of a cell passing through an electric field where a constant current is maintained delivering a signal which is interpreted so as to obtain information about the volume of the cell passing through this field and using at least partially an optical method which consists in causing a cell to pass through a light ray and collecting in an optical reader the light absorbed by the cell so as to provide a signal interpreted so as to obtain information about the absorbance of the cell, which apparatus comprises essentially a case for injecting the flow of sample to be analyzed inside a measurement tank, through which passes a light beam collected by a sensor, the sample flow being sleeved hydrodynamically inside the tank by at least one pressurized sleeving liquid injected into the tank through at least one feed duct, in which apparatus the electrodes for measurement of the resistivity of the leucocytic sub-population are component elements of the injection case, and in which circuits for preparing and feeding the sample flow and sleeving liquids are provided upstream of the injection case, whereas units for collecting and processing the signals delivered by the optical sensor and said electrodes are provided downstream of the injection case, the information being processed by a computer and restored graphically and/or digitally.

According to a characteristic of the invention, an external injection nozzle is mounted inside the case and ends in a calibrated orifice which causes the internal chamber of said nozzle to communicate with the tank, for emitting a first sleeving liquid.

Advantageously, an annular chamber is formed between a conical part of the external injection nozzle and an internal face of the case; it communicates with the measurement tank and is fed with pressurized fluid through at least one duct.

According to another particular characteristic of the invention, an internal injection nozzle is mounted inside the external nozzle and has an orifice for the injection of pressurized fluid coming from a duct which opens into a chamber inside said external nozzle in line with the calibrated orifice.

The invention also provides for glass walls on each side of the measurement tank which are surrounded, on one side, by a lamp and, on the other, by a sensor which receives the beam emitted by the lamp and focussed by optical elements, which has passed through the sleeved flow of the solution to be analyzed, passing into the tank.

Furthermore, the resistivity measurement electrodes are formed on the one hand by the end piece of the discharge duct for the sleeved flow of solution leaving the tank and, on the other hand, by the internal nozzle for injection of the solution to be analyzed.

Interpretation of the results delivered by the analysis is advantageously obtained in accordance with the invention by the fact that the information coming from the resistivity measurements is restored in the form of a curve of distribution of the sizes for localizing, between a low threshold and a high threshold, the main leucocytic population, by separating the stromata and platelets as well as the very large sized particles.

Similarly, the information coming from the optical measurements are restored by means of an absorbance distribution curve for localizing, between a low threshold and a high threshold, the absorbance of the leucocytes by separating the little absorbent cell populations and the intense absorption cell populations.

In addition, it seems advantageous also for the information from the resistivity measurements and optical measurements to be restored in a graphic representation of matrix form, for displaying the contours representative of the distribution of the populations. Other characteristics and advantages of the invention will be better understood from the following description with reference to the accompanying drawings which show:

DETAILED DESCRIPTION OF THE INVENTION

Figure 1:
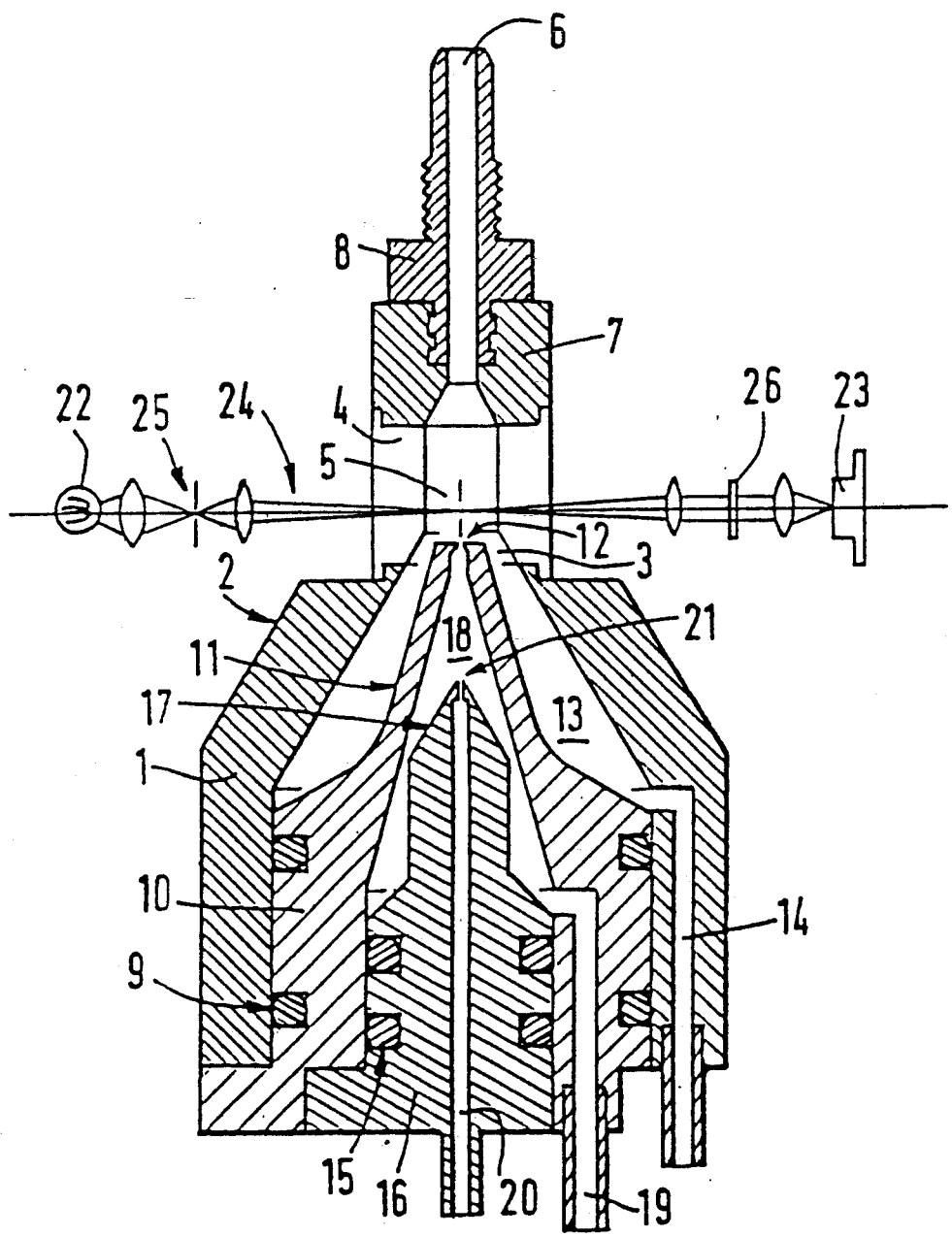
FIG. 1, a sectional view of the injection case.

The apparatus shown in FIG. 1 comprises an injection case 1 of general cylindrical shape whose upper part has a conical profile 2. Orifice 3 of case 1 is covered, on at least two opposite faces, with glass walls 4 between which is disposed a measurement tank 5 communicating by its nozzle with the injection case and opening at its upper part into a discharge duct 6. A plug 7, applied on the glass walls 4, holds tank 5 in position and also serves for supporting the end piece 8 of the discharge duct.

Inside the injection case 1 is sealingly mounted, via O-seals 9, an external injection nozzle 10 whose upper end 11 of conical shape opens at the base of the measurement tank 5. It ends in a calibrated orifice 12, for example a hole jewel, which causes the inner chamber 18 of said nozzle to communicate with tank 5. It will be noted that between the internal face of the conical part 2 of the injection case and the external face of the conical end 11 of nozzle 10 is formed an annular chamber 13 which also communicates with the measurement tank. This chamber 13 is fed with pressurized fluid through a duct 14.

Inside the external injection nozzle 10 is sealingly mounted via O-seals 15 an internal injection nozzle 16 whose upper end 17, also of a conical shape, extends into the inner chamber 18 of the external nozzle 10, below the calibrated orifice 12. Chamber 18 is itself fed with pressurized fluid through a duct 19. Similarly, the internal nozzle has passing therethrough a duct 20 for injecting pressurized fluid through orifice 21 of said nozzle, in line with the calibrated orifice 12. The two glass walls 4 are surrounded, on one side by a lamp 22 and on the other by a sensor 23 so that the light beam 24 emitted by the lamp and focussed by an appropriate optical projector 25 passes through these walls and the measurement tank 5 and is collected by the sensor after passing through another optical system 26.

The leucocyte solution to be analyzed is injected through the central duct 20 and escapes through orifices 21 into chamber 18. Simultaneously, a pressurized liquid called "sleeving liquid" is injected through duct 19 for providing hydrodynamic sheathing of the solution in the calibrated orifice 12. The sleeved flow from this first sleeving passes then through the calibrated orifice 12 and is then subjected to a second sleeving provided by injection of pressurized liquid through duct 14 and oriented inside the annular chamber 13. This sleeving emerges through orifice 13 into the measurement tank 5 through which passes, perpendicularly to the flow, a light beam 24, concentrated and focussed on the leucocyte solution flow. The circulation of the flows in the measurement assembly takes place from bottom to top, along a vertical axis, thus avoiding the stagnation of possible bubbles. The fact of thus using double sleeving has a number of advantages.

The first sleeving provides perfect centering of the flow of cells through the counting orifice and, because of the fineness of the flow formed and of the dilution ratio, prevents the coinciding passage of several cells. The phenomena of deformation of the cells due to the edge effects as well as bouncing of the cells in the sensitivity zone of the counting orifice are also eliminated.

The second sleeving envelopes the flow leaving the orifice and maintains it concentric and stabilized over the whole path in the optical tank, thus making several readings possible at different angles and at different levels.

The second sleeving makes it possible to use an optical reading tank with wide inner passage eliminating the turbulences of edge effects and the risk of fouling up which would make the flow unstable and the optical quality mediocre.

The fact of using a large sized tank also eliminates the speed of the flow on these walls: since this speed is low, the erosion of the glass walls—which can be observed over a long period on capillary optical tanks in which the speed of the sleeve must be equal to the speed of the flow—is reduced. The cumulation of these characteristics added to the fact that the positioning of the flow is provided by positioning the counting orifice, makes the alignment of the optical beam on the flow extremely stable. Dismantling of the tank does not necessitate optical adjustment after re-assembly.

Counting and detection of the volume are provided by resistivity measurements. For this, a current is applied to the terminals of two electrodes situated on each side of orifice 12, namely an anode formed by end piece 8 of the discharge duct and a cathode formed of the internal injection nozzle 16. Counting of the leucocytes is then carried out during passage of the solution through the calibrated orifice 12, each cell passing through the orifice causes an increase of the resistivity of the medium situated between the electrodes 8, 16, thus creating a voltage pulse proportional to the volume of the leucocyte. The optical detection, i.e. the determination of the intensity of absorption of the leucocytes, is measured by means of the light beam 24 passing through tank 5 perpendicularly to the flow to be analyzed. The light beam is provided by means of lamp 22, whose light energy passing through a filter of a wavelength corresponding to the absorption of the cell, then a window is concentrated on a diaphragm behind which the optical projector assembly 25 is placed, focussed on the leucocyte solution flow. The image of the light window, through which the flow of solution passes, passes through a collimator then is projected by the other collecting optical system 26 on a photodiode 23 to the terminals of which is connected an amplifier circuit.

Each leucocyte passing through the light beam causes a reduction of the light intensity measured on the photodiode, proportional to the intensity of its absorption. That results in an electric pulse at the terminals of the amplifier, whose amplitude is itself proportional to the optical density of the leucocyte.

The calibrated orifice 12 is, as shown in FIG. 1, slightly spaced apart from the light beam 24 passing through the tank. It will be noted that this distance separating orifice 12 from the optical measurement focussing point generates a time shift of the resistive and optical pulses. The constancy of this shift is controlled and makes it possible to show the least drop in the performance of the fluidics.

The micro-bubbles are naturally eliminated from the counting by the resistance to the vertical flow which the air bubble opposes, thus generating a shift in the resistive and optical counts greater than the standard shift generated by a cell.

To be taken into account, a blood cell must, previous to the optical measurement, be measured resistively by its passage through the calibrated orifice 12. Thus, the particles possibly contained in the injected liquid sleeve after the counting orifice cannot be taken into account since they have not generated a resistive pulse.

Before going ahead with injecting blood into the above described apparatus, it is advisable to prepare the blood sample to be analyzed so as to obtain a solution containing mainly the leucocytes in their most natural possible form. If necessary, the cells may be specifically coloured by a given cytochemical means.

Figure 2:
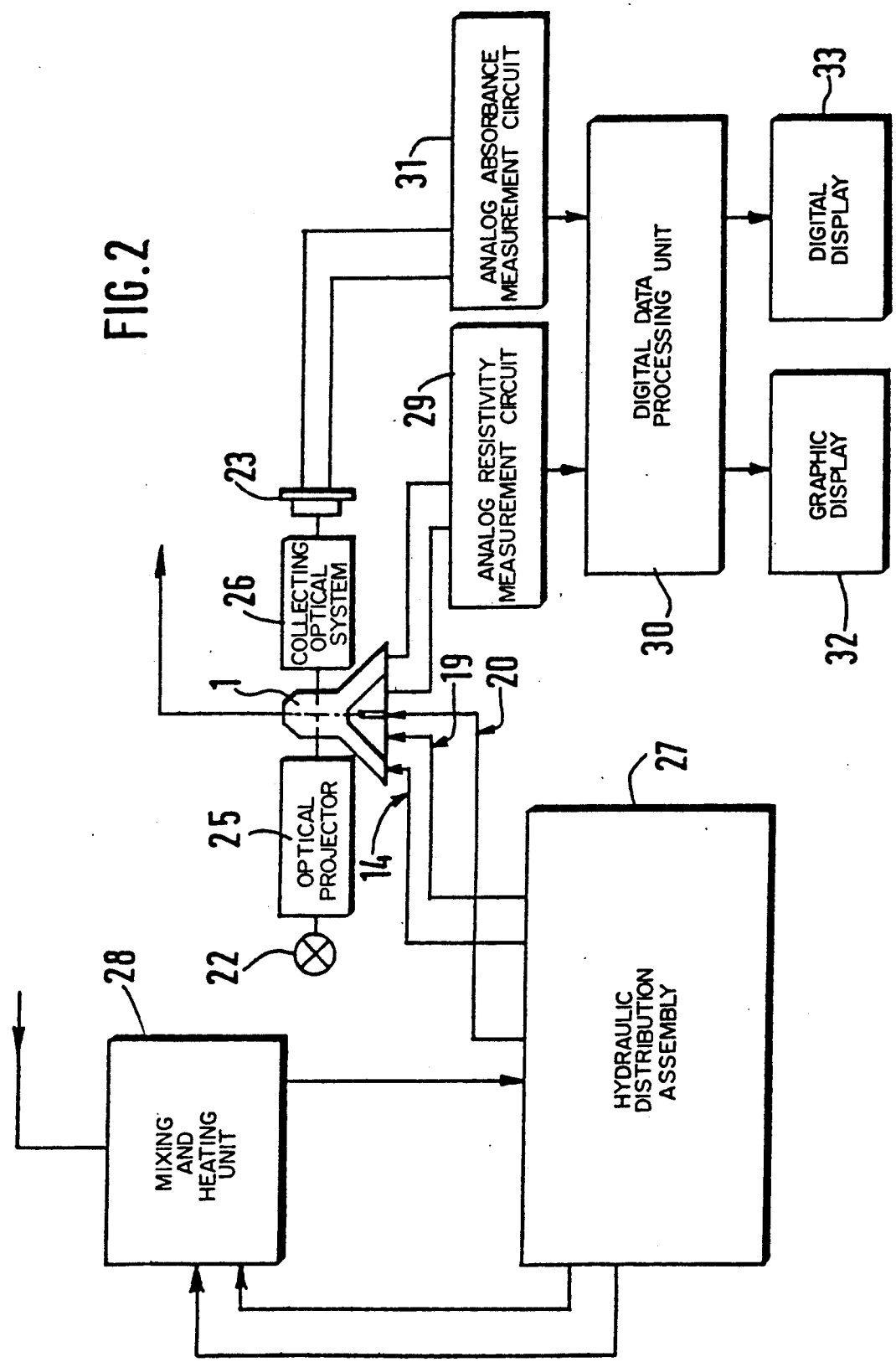
FIG. 2, a schematic view of the preparation and processing circuits associated with the apparatus, FIG. 3, a curve of distribution of the sizes of the analyzed leucocytes, FIG. 4, a curve of distribution of the absorbances of the analyzed leucocytes, and FIG. 5, a graphic matrix representation of the contours representative of the populations.

In FIG. 2, the processing circuits have been shown associated with the apparatus of FIG. 1. The case 1 has been shown schematically and its associated optical assembly formed of lamp 22, the optical projector 25, the collecting optical system 26 and the reception photodiode 23. The blood fed into case 1 by duct 20 as well as the sleeving fluids fed through ducts 14 and 19, undergo preparation and come from a hydraulic distribution assembly 27, itself fed with a blood sample coming from a mixing and heating unit 28. The electrodes located in case 1 deliver signals proportional to the volume of the leucocytes received in an analog resistivity measurement circuit 29, which signals are converted into a digital value in a digital data processing unit 30. Photodiode 23 delivers signals proportional to the optical density of the leucocytes received in an analog absorbance measurement circuit 31, which signals are also processed in unit 30 which then delivers graphic 32 or digital 33 results. The set of signals from the same sample is processed by means of a computer so as to determine the number of leucocytes counted in a pre-established time as well as relative values of volume and optical density for each of them.

When the processed blood solution passes through the measurement apparatus 1, each cell causes alternately a pulse proportional to its size when it passes through the calibrated orifice 12, then a pulse proportional to its absorbance during its passage through the light beam 24. For the same cell, a volume value and an absorbance value are stored and the total results of the volumes and absorbances are distributed in the form of a histogram.

Figure 3:
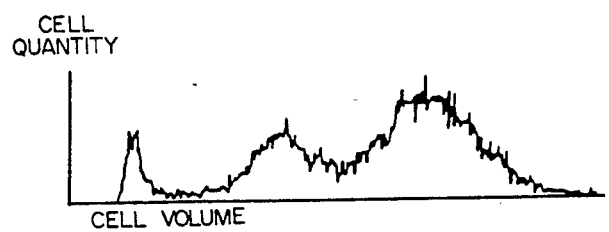

On a curve of distribution of the sizes, shown by way of example in FIG. 3, with the quantitative representation in ordinates and the volume in abscissa, the presence of three distinct populations will be noted. The most leftward population, so of small sized particles, is considered as being the background noise formed mainly of stromata, resultants of the hemolysis and of the platelets.

Figure 4:
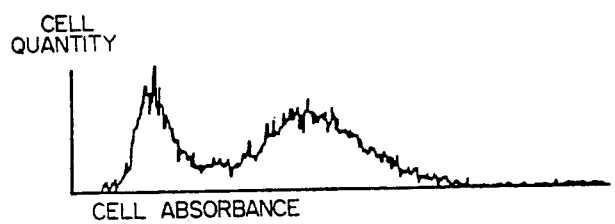

The other two right-hand populations are considered as being the whole of the leucocytes in the sample analyzed. In a distribution curve of the absorbances also shown by way of example in FIG. 4, a first population is obtained on the left formed of cells which are little or only slightly absorbent, a second central population formed of cells with average absorbance and a third population on the right formed of high absorbance cells.

Figure 5:
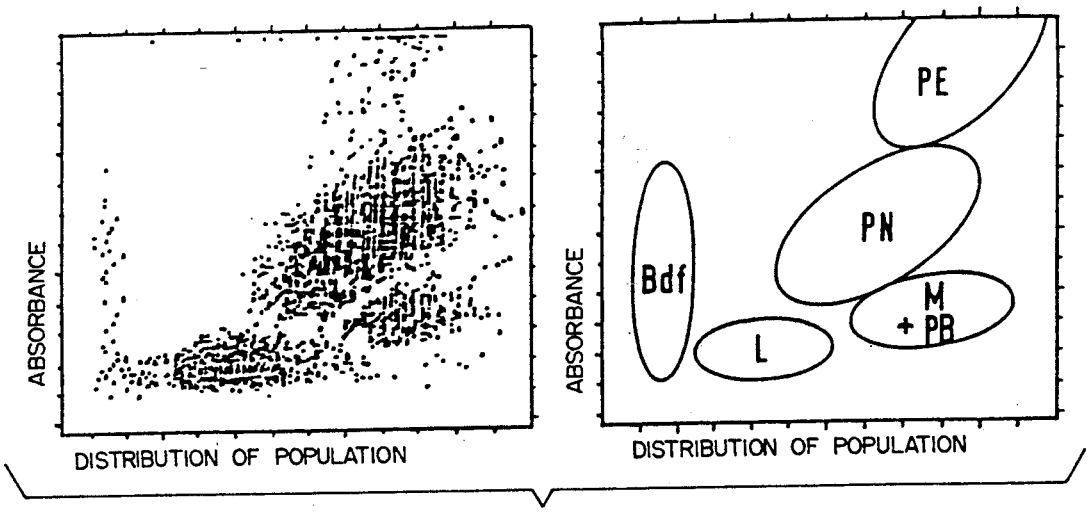

On a matrix graphic representation also shown by way of example in FIG. 5, the distribution of the populations can be observed in size along the X axis and in absorbance along the Y axis. This representation makes it possible to study the leucocytes by means of a taxonomy software, the positioning of the thresholds permitting the separation of at least one leucocyte population, Bdf representing the background noises (stromata and platelets):

L : Lymphocytes
M : Monocytes
PN : Polynuclear neutrophils
PE : Polynuclear eosinophils
PB : Polynuclear basophils.

The invention is not limited to the embodiments described nor to this type of analysis. Particularly, by replacing the optical filter by a filter wheel, it will be possible to read multiple colorations for analyzing other cell types.

In addition, mention was made above of an optical measurement tank. In a variant of construction, it would be possible to measure the light diffraction of a cell passing through this tank. One or more sensors being disposed focussed on the tank, in the alignment of a light ray passing therethrough. The information collected, depending on whether the total diffraction or diffractions at several angles are measured, makes it possible to determine either the relative size of the cell or, in the case of two diffraction measurements at different angles, the size and the relative optical density.

In a variant, it would also be possible to make a cytofluorescent measurement by positioning a sensor assembly focussed on the measurement tank, at 90° from the laser ray passing through it. The assembly for preparing the sample must be adapted so as to obtain the desired cell fluorescence. The measurements thus obtained make it possible to evaluate the volume of the cell by resistivity, and its fluorescence.

In a further variant, still according to the same principle of the measurement assembly, the current applied to the electrodes and flowing through the counting orifice, may be a high frequency current for obtaining, depending on the form of the pulses collected, identification of the internal composition of the cell, namely the relative size of the nucleus, denser with respect to the external envelope (cytoplasm) of the cell.

The combination of the above variants makes it possible to obtain, for a flow of cells passing through the measurement tank, both the overall volume of each cell associated with its optical density and/or its fluorescence, as well as information about is internal composition, namely the relative size of its nucleus and/or its relative form or its regularity.

We claim:

1. Apparatus for counting and determining at least one leucocytic sub-population by resistivity based on the principle of a cell passing through an electric field where a constant current is maintained delivering a signal providing information about the volume of the cell passing through this field and using an optical method wherein a cell passes through a light ray and light absorbed by the cell is collected in an optical reader to provide information about the absorbance of the cell, said apparatus comprising a case for injecting a flow of sample to be analyzed inside a measurement tank though which passes a light beam collected by a sensor, characterized in that the sample low is sleeved hydrodynamically inside the tank by at least first and second pressurized sleeving liquids injected through the tank through at least two separate feed ducts, the second sleeving liquid flow enveloping the first sleeving liquid flow, wherein an external injection nozzle terminating in a calibrated orifice is mounted inside the case and causes an internal chamber of said nozzle to communicate with the tank, for emitting the first sleeving liquid, and wherein electrodes for measurement of the resistivity of the leucocytic sub-population are component elements of the injection case, circuits for preparing and feeding the sample flow and sleeving liquids are provided upstream of the injection case, and units for collecting and processing the signals delivered by the optical sensor and said electrodes are provided downstream of the injection case, information obtained being processed by a computer and processed information provided to a user.

2. Apparatus according to claim 1, characterized in that the information from the resistivity measurements and optical measurements is provided in a graphic representation of matrix form, for displaying the contours representative of the distribution of the populations.

3. Apparatus according to claim 1, characterized in that the calibrated orifice is offset from the light beam passing through the tank.

4. Apparatus according to claim 1, characterized in that an annular chamber is formed between a conical part of the external injection nozzle and an internal face of the case and said chamber communicates with the measurement tank and is fed with pressurized fluid through a duct for the emission of the second sleeving liquid.

5. Apparatus according to claim 1, characterized in that an internal injection nozzle is mounted inside the external nozzle and has an orifice for the injection of pressurized fluid coming from a duct which opens into a chamber inside said external nozzle in line with the calibrated orifice.

6. Apparatus according to claim 1, using a measurement tank having, on one side, a lamp emitting the light beam and, on the other side, a sensor which receives the light beam emitted by the lamp and focussed by optical elements, characterized in that the measurement tank comprises an internal passage of sufficient width that the doubly sleeved flow remains concentric and stabilized during its travel through the tank.

7. Apparatus according to claim 1, characterized in that the light beam comprises a laser ray and a sensor assembly is positioned, focussed on the measurement tank, at 90° from a laser ray passing through it, for carrying out a cytofluorescence measurement.

8. Apparatus according to claim 1, characterized in that the resistivity measurement electrodes are formed by an end piece of the discharge duct for the sleeved flow of solution leaving the tank, forming the anode, and by the internal nozzle for injection of the solution to be analyzed, forming the cathode.

9. Apparatus according to claim 1, characterized in that the liquid to be analyzed and the sleeving fluids come from a hydraulic distribution assembly fed by a sample from a mixing and heating unit.

10. Apparatus according to claim 1, characterized in that the information from the resistivity measurements is provided in the form of a curve of distribution of volumes for localizing a main leucocytic population.

11. Apparatus according to claim 1, characterized in that the information from the optical measurements is provided by means of an absorbance distribution curve for localizing the absorbance of the leucocytes.

* * * * *